United States Patent [19]
Rybczynski et al.

[11] Patent Number: 5,510,489
[45] Date of Patent: Apr. 23, 1996

[54] METHOD OF PREPARING 1-AMINO-2, 6-DIMETHYLPIPERIDINE

[75] Inventors: Wolfgang Rybczynski, Rodenbach; Wolfgang Bauer; Eckard Kujath, both of Maintal; Manfred Schrod, Weiterstadt, all of Germany

[73] Assignee: Cassella Aktiengesellschaft, Frankfurt am Main, Germany

[21] Appl. No.: 244,142

[22] PCT Filed: Nov. 12, 1992

[86] PCT No.: PCT/EP92/02594

§ 371 Date: May 17, 1994

§ 102(e) Date: May 17, 1994

[87] PCT Pub. No.: WO93/10110

PCT Pub. Date: May 27, 1993

[30] Foreign Application Priority Data

Nov. 20, 1991 [DE] Germany .......................... 41 38 143.2

[51] Int. Cl.⁶ .................................................. C07D 711/98
[52] U.S. Cl. ................................................................ 546/244
[58] Field of Search ............................................... 546/244

[56] References Cited

U.S. PATENT DOCUMENTS 2,979,505  4/1961  Tuemmler et al. .................. 260/347.5

FOREIGN PATENT DOCUMENTS 1545552  8/1965  Germany .

OTHER PUBLICATIONS

Chemical Abstracts, vol. 110, p. 709, No. 154163g (1989).
Chemical Abstracts, vol. 112, p. 495, No. 20,909n (1990).
Chemical Abstracts, vol. 112, p. ? No. 216,712n (1989).
Chemical Abstracts, vol. 112, p. ? No. 216,713p (1987).
Chemical Abstracts, vol. 112, p. ? No. 216,714q (1989).
Chemical Abstracts, vol. 110, pp. 733, No. 192,658e.
Chemical Abstracts, vol. 110, p. 733, No. 192,659f.
Tensid–Taschenbuch, Stache et al, pub. by Carl Hanser, Munich Germany, 1991 pp. 22–28, 55–58.
Rompps Chemie Lexikon, Neumuller, pub. by Franckh'sche Verlagshandlung, 1983, pp. 1786.

*Primary Examiner*—C. Warren Ivy
*Assistant Examiner*—Raymond Covington
*Attorney, Agent, or Firm*—Perman & Green

[57] ABSTRACT

The present invention relates to improved processes for the preparation of 1-amino-2,6-dimethylpiperidine whereby the yield is more than 90%. The processes involve the hydrogenation of 1-nitroso-2,6-dimethylpiperidine in the presence of a palladium catalyst which is partly poisoned with iron ions, in an aqueous solvent, and are characterized by the inclusion of at least one surfactant. The surfactant preferably is anionic or nonionic.

13 Claims, No Drawings

METHOD OF PREPARING 1-AMINO-2, 6-DIMETHYLPIPERIDINE

This is the U.S. National Stage application of PCT/EP92/02594 filed Nov. 12, 1992.

The invention relates to a process for the preparation of 1-amino-2,6-dimethylpiperidine.

1-Amino-cis-2,6-dimethylpiperidine is a key intermediate product in the synthesis of the loop saluretic clopamide (4-chloro-N-(cis-2,6-dimethylpiperidino) sulfamoylbenzamide) and the cardiovascular agent pirsidomine (3-(cis-2,6-dimethylpiperidino)-N-(4-methoxybenzoyl)sydnonimine).

All the known preparation processes for 1-amino- 2,6-dimethylpiperidine are based on reduction of 1-nitroso-2,6-dimethylpiperidine. All these have an incomplete conversion and, above all, have ecological deficiencies.

Furthermore, the production of large amounts of waste salts in the reduction with sodium dithionite (C. G. Overberger, J. G. Lombardine and R. G. Hiskey, J. Org. Chem. 22 (1957) 858) is a disadvantage.

The use of zinc in dilute acetic acid as a reducing agent (E. Jucker and A. Lindemann, Helv. Chim. Acta, 45 (1962) 2316–2325, in particular 2323) leads to considerable heavy metal pollution of the waste water formed.

The reduction with complex hydrides, such as lithium aluminum hydride in ether (C. G. Overberger, L. C. Palmer, B. S. Marks and N. R. Byrd, J. Am. Chem. Soc. 77 (1955) 4100) or bis(2-methoxyethoxy) sodium aluminum hydride in toluene (M. Londyn and M. Borovicka, Czechoslovakian Patent 253243, applied for on 21.01.1986) cannot be carried out on a larger scale for safety reasons.

A process is known from USP 2 979 505 for the preparation of substituted hydrazincs, such as, for example, N-aminopiperidine, in which the corresponding nitroso amines are hydrogenated in the presence of a palladium catalyst which contains a certain amount of a soluble iron salt. According to the Hungarian Patent Specification 15614, the preparation of 1-amino-cis-2,6-dimethylpiperidine by this process is unsatisfactory both in respect of the yield (65%) and in respect of the selectivity (60 to 70%). According to the process of Hungarian Patent Specification 15614, 1-amino-cis-2,6-dimethylpiperidine is therefore prepared by nitrosation of cis-2,6-dimethylpiperidine and hydrogenation of the resulting nitroso compound in aqueous ammoniacal solution in the presence of a palladium catalyst poisoned with an Fe(II) salt, the two reactions being carried out in the absence of chloride ions. This process has considerable problems both in the reaction and in the working up of the reaction mixture obtained. Thus, for example, the use of ammonia requires additional process technology measures to avoid corrosion and emission. The amount of ammonia used furthermore is high (100 to 150 g of ammonia per 1 kg of product). Nevertheless, the main problem here, as also in the case of the other processes, is the incomplete conversion, which causes the product to contain still unreacted 1-nitroso-2,6-dimethylpiperidine. In the process of Hungarian Patent Specification 15614, this amount is still at least 3%.

The object of the present invention was therefore to provide a process for the preparation of 1-amino-2,6-dimethylpiperidine by reduction of 1-nitroso-2,6-dimethylpiperidine which does not have the disadvantages of the processes which have been disclosed to date and by which, in particular, a complete conversion is achieved.

The invention thus relates to a process for the preparation of 1-amino-2,6-dimethylpiperidine by catalytic hydrogenation of 1-nitroso-2,6-dimethylpiperidine using a palladium catalyst partly poisoned with iron ions. The process according to the invention is characterized in that it is carried out in an aqueous solvent in the presence of a surfactant or mixture of surfactants.

Aqueous solvents which can be used are mixtures of water with water-miscible organic solvents, such as, for example, alcohols, glycols, glycol ethers and the like. Water is preferably used as the aqueous solvent.

Surfactants are classified into anionic, nonionic, cationic and amphoteric types, of which the anionic and nonionic types are particularly preferred in the process according to the invention. Suitable anionic surfactants are, for example, sulfonated aromatic hydrocarbons, such as the sodium salt of dodecylbenzenesulfonic acid; sulfonated aliphatic hydrocarbons, such as the sodium salt of sec-pentadecanesulfonic acid; sulfonated α-olefins, such as the sodium salt of α-hexadecenesulfonic acid; sulfated fatty alcohols, such as sodium lauryl sulfate; sulfated fatty alcohol ethers, such as sodium lauryl polyglycol ether-sulfate; sulfonated fatty acid methyl esters, such as palm kernel sulfo-fatty acid methyl ester Na salt; and carboxymethylated fatty alcohol polyglycol ethers, such as lauryl polyglycol etheracetate Na salt.

Suitable nonionic surfactants are, for example, fatty alcohol oxyethylates, alkylphenol oxyethylates, fatty acid oxyethylates, fatty acid alkylolamides, fatty amine oxyethylates, polyalkylene oxide block polymers, fatty acid esters of sorbitan and ethoxylated fatty acid esters of sorbitan.

Suitable surfactants, also called emulsifiers or detergents, for example, depending on their intended use, are marketed by numerous companies. A surfactant having a low foaming capacity, good environmental compatibility and good biological degradability is preferably employed.

In carrying out the process according to the invention, preferably 0.1 to 10% by weight, especially preferably 1 to 6% by weight, of surfactant or mixture of surfactants is added to the aqueous solvent, in particular to the water.

The palladium catalyst is preferably employed in an amount such that the amount of Pd is 0.1 to 10 mol%, based on the 1-nitroso-2,6-dimethylpiperidine.

Palladium catalysts which are used are, in particular, those in which the palladium is adsorbed onto a support, preferably charcoal or aluminum oxide, and which have a Pd content of 1 to 10% by weight.

The catalyst is partly poisoned by the addition of a soluble iron salt before or during the reaction. Fe(II) sulfate is a particularly suitable soluble iron salt here. The molar ratio of Pd:Fe is preferably (20 to 0.5):1.

The hydrogenation is carried out at normal temperature or preferably elevated temperature, for example at 20° to 80° C., and, for example, under a hydrogen pressure of 1 to 100 bar. A reaction temperature of 30° to 50° C. and/or a hydrogen pressure of 2 to 25 bar is particularly preferred here.

Surprisingly, a practically complete conversion of more than 99% is achieved by the process according to the invention. The starting substance 1-nitroso-2,6-dimethylpiperidine employed is detectable in the reaction product, if at all, only in traces using sensitive detection methods.

The reaction mixture which, in the process according to the invention, remains after removal of the catalyst by filtration generally comprises, based on the 1-nitroso-2,6-dimethylpiperidine employed, more than 90% of 1-amino-2,6-dimethylpiperidine, 9% of 2,6-dimethylpiperidine and, as already mentioned, not more than traces of 1-nitroso-2,6-dimethylpiperidine. The selectivity is therefore 90%. By rectification, preferably under reduced pressure, some of the by-product and the water can be removed as the top product. The substances which then still remain in the bottom product in addition to the desired 1-amino-2,6-dimethylpiperidine (by-product, water and surfactant) cause no trouble during further processing.

Over the same hydrogenation times as in the process of Hungarian Patent Specification 15614, a more complete conversion is achieved, with ammonia being completely avoided.

The process according to the invention is equally suitable for the preparation of 1-amino-cis-2,6- or trans-2,6-dimethylpiperidine.

EXAMPLE 1

An autoclave (volume 1 l) is charged with 114 g of 1-nitroso-cis-2,6-dimethylpiperidine, 8 g of Pd/C catalyst (10% strength), 2 g of $FeSO_4 \times 7H_2O$, 100 ml of distilled water and 3 g of surfactant Hostapur®SAS 93 (n $C_{13}$ to $C_{17}$ alkanesulfonate Na salt from Hoechst AG, Frankfurt am Main 80). At 40° C. under a hydrogen pressure of 6 bar, the hydrogenation has ended after 5 hours.

After the catalyst has been removed by filtration, the reaction mixture contains (based on the 1-nitroso-2,6-dimethylpiperidine employed) more than 90% of 1-amino-2,6-dimethylpiperidine, 9% of cis-2,6-dimethylpiperidine and 1-nitroso-cis-2,6-dimethylpiperidine only in traces which are detectable by gas chromatography (conversion >99%; selectivity=90%).

By rectification, some of the by-product and the water can be removed. The substances remaining in the product (by-product, water and surfactant) do not manifest themselves adversely during its further use.

EXAMPLE 2

On repetition of Example 1, the Hostapur®SAS 93 is replaced by 3 g of the surfactant Emulgator NW (aryl polyglycol ether, manufacturer Bayer AG, Leverkusen). The conversion and the selectivity are equally as good as those in Example 1.

EXAMPLE 3

On repetition of Example 1, the Hostapur®SAS 93 is replaced by 3 g of the surfactant Dispersogen®P (from Hoechst AG, Frankfurt am Main). The conversion and the selectivity are similarly good to those in Example 1.

EXAMPLE 4

On repetition of Example 1, the 8 g of Pd/C catalyst and the 2 g of $FeSO_4 \times 7H_2O$ are replaced by a catalyst prepared as follows: 8 g of Pd/C catalyst (10% strength) and 2 g of $FeSO_4 \times 7H_2O$ are stirred in 100 ml of distilled water under a nitrogen atmosphere for 1 hour. The partly poisoned catalyst is then filtered off and dried by suction.

We claim:

1. In the process for the preparation of 1-amino-2,6-dimethylpiperidine by catalytic hydrogenation of 1-nitroso-2,6-dimethylpiperidine in the presence of a palladium catalyst partly poisoned with iron ions, the improvement which comprises increasing the yield to more than about 90% by carrying out the hydrogenation in an aqueous solvent containing from about 0.1 to 10% by weight of at least one surfactant.

2. Process according to claim 1, in which the aqueous solvent is water.

3. Process according to claim 1, in which the surfactant is an anionic surfactant.

4. Process according to claim 1, in which the aqueous solvent contains 1 to 6% by weight, of at least one surfactant.

5. Process according to claim 1, in which the palladium catalyst is present in an amount such that the amount of Pd is 0.1 to 10 mol%, based on the 1-nitroso-2,6-dimethylpiperidine.

6. Process according to claim 1, in which the hydrogenation is carried out at a temperature of 20° to 80° C., and/or under a hydrogen pressure of 1 to 100 bar.

7. Process according to claim 1 in which the palladium catalyst is a supported catalyst having a Pd content of 1 to 10% by weight.

8. Process according to claim 1, in which the ratio of Pd:Fe is (20 to 0.5):1.

9. Process according to claim 1, in which 1-nitroso-cis-2,6-dimethylpiperidine is employed as the starting substance.

10. Process according to claim 1 in which the surfactant is a nonionic surfactant.

11. Process according to claim 6 in which the temperature is between 30° to 50° C. and the hydrogen pressure is between 2 to 25 bar.

12. Process according to claim 7 in which the supported catalyst is a Pd/C catalyst.

13. Process according to claim 7 in which the supported catalyst is a $Pd/Al_2O_3$ catalyst.

* * * * *